(12) United States Patent
Himeno

(10) Patent No.: US 11,264,127 B2
(45) Date of Patent: Mar. 1, 2022

(54) INTEGRATED MULTI-FACILITY DOCUMENT MANAGEMENT SYSTEM

(71) Applicant: IRYOU JYOUHOU GIJYUTU KENKYUSYO CORPORATION, Fukuoka (JP)

(72) Inventor: Shinkichi Himeno, Fukuoka (JP)

(73) Assignee: IRYOU JYOUHOU GIJYUTU KENKYUSYO CORPORATION, Fukuoka (JP)

( * ) Notice: Subject to any disclaimer, the term of this patent is extended or adjusted under 35 U.S.C. 154(b) by 1062 days.

(21) Appl. No.: 15/747,384

(22) PCT Filed: Jul. 20, 2016

(86) PCT No.: PCT/JP2016/071204
§ 371 (c)(1),
(2) Date: Jan. 24, 2018

(87) PCT Pub. No.: WO2017/018277
PCT Pub. Date: Feb. 2, 2017

(65) Prior Publication Data
US 2018/0218786 A1    Aug. 2, 2018

(30) Foreign Application Priority Data

Jul. 28, 2015  (JP) .............................. JP2015-148922

(51) Int. Cl.
*G16H 40/20*    (2018.01)
*G06F 21/31*    (2013.01)
(Continued)

(52) U.S. Cl.
CPC ............. *G16H 40/20* (2018.01); *G06F 16/93* (2019.01); *G06F 21/31* (2013.01);
(Continued)

(58) Field of Classification Search
CPC ......... G16H 40/20; G06F 16/93; G06F 21/31; G06F 21/6245
See application file for complete search history.

(56) References Cited

U.S. PATENT DOCUMENTS

| 7,062,532 B1* | 6/2006 | Sweat .................... G06Q 10/06 709/205 |
| 2006/0218394 A1* | 9/2006 | Yang ..................... G06F 21/604 713/167 |
| 2007/0006322 A1* | 1/2007 | Karimzadeh ......... G06F 21/604 726/27 |

FOREIGN PATENT DOCUMENTS

| JP | 2000-207336 | 7/2000 |
| JP | 2002-207829 | 7/2002 |

(Continued)

OTHER PUBLICATIONS

EClinicalWorks, System Administration Guide, Nov. 2014, v10, p. 15-295 (Year: 2014).*

(Continued)

*Primary Examiner* — Evangeline Barr
(74) *Attorney, Agent, or Firm* — Hamre, Schumann, Mueller & Larson, P.C.

(57) ABSTRACT

An integrated multi-facility document management system is configured to allow an access right attribute to be dragged and dropped from one tree form to a root of a another tree form whereby when the access right attribute is dragged and dropped from the one tree form to the root of the other tree form a corresponding access right attribute of the root is changed to the access right attribute and a corresponding access right attribute in branches connected to the root is changed to the access right attribute.

4 Claims, 7 Drawing Sheets

(51) Int. Cl.
   *G06F 21/62* (2013.01)
   *G06F 16/93* (2019.01)
   *G06Q 10/10* (2012.01)
   *G16H 10/60* (2018.01)
   *G16H 40/67* (2018.01)

(52) U.S. Cl.
   CPC ......... *G06F 21/6245* (2013.01); *G06Q 10/10* (2013.01); *G16H 10/60* (2018.01); *G16H 40/67* (2018.01)

(56) References Cited

FOREIGN PATENT DOCUMENTS

| JP | 2004-062780 | 2/2004 |
|----|-------------|--------|
| JP | 2006-085356 | 3/2006 |
| JP | 2007-233635 | 9/2007 |
| JP | 2009-070206 | 4/2009 |

OTHER PUBLICATIONS

Jonas Schulte, et al., Enhanced Security Management for Flexible and Dynamic Cooperative Environments, 2009, 10.4IOBI/CST.collaboratecom2009. B377 (Year: 2009).*

System Administration Guide, Nov. 2014, v10, p. 15-295 (Year: 2014).*

Johnas Schulte, et al., Enhanced Security Management for Flexible and Dynamic Cooperative Environments, 2009, 10.4IOBI/CST.collaboratecom2009. B377 (Year: 2009).*

Shinkichi Himeno, U.S. Appl. No. 15/574,694, filed Nov. 16, 2017 (38 pages).

International Search Report and Written Opinion, International Patent Application No. PCT/JP2016/071204, with English translation of Search Report, dated Oct. 11, 2016 (6 pages).

* cited by examiner

Fig.1- Prior Art

| TYPES OF JOBS | DOCTOR ARTICLE LINE | DOCTOR ORDER LINE | NURSING ARTICLE LINE | CARE ARTICLE LINE |
|---|---|---|---|---|
| DOCTOR | ○ | ○ | △ | △ |
| NURSE | △ | △ | ○ | △ |
| CAREGIVER | × | × | △ | ○ |
| ... | ... | ... | ... | ... |

Fig.4

| | A HOSPITAL | | | | B CARE FACILITY | | | | C PAY NURSING HOME MR. YAMADA | | | | HOME MR. ARIMURA | | | |
|---|---|---|---|---|---|---|---|---|---|---|---|---|---|---|---|---|
| | DOCTOR ARTICLE LINE | DOCTOR ORDER LINE | NURSING ARTICLE LINE | CARE ARTICLE LINE | DOCTOR ARTICLE LINE | DOCTOR ORDER LINE | NURSING ARTICLE LINE | CARE ARTICLE LINE | DOCTOR ARTICLE LINE | DOCTOR ORDER LINE | NURSING ARTICLE LINE | CARE ARTICLE LINE | DOCTOR ARTICLE LINE | DOCTOR ORDER LINE | NURSING ARTICLE LINE | CARE ARTICLE LINE |
| 0943 DOCTOR OF A HOSPITAL DOCTOR RESPONSIBLE FOR MR. ARIMURA AT HOME | O | O | △ | △ | △ | △ | △ | △ | × | × | × | × | O | O | △ | △ |
| 1285 DOCTOR OF C HOME CLINIC RESPONSIBLE FOR MR. YAMADA IN C PAY NURSING HOME | × | × | × | × | × | × | × | × | O | O | △ | × | × | × | × | × |
| 2513 NURSE OF A HOSPITAL | △ | △ | O | △ | △ | △ | △ | △ | × | × | × | × | × | × | × | × |
| 4165 NURSE OF E HOME NURSING STATION RESPONSIBLE FOR MR. YAMADA IN C PAY NURSING HOME AND MR. ARIMURA AT HOME | × | × | × | × | × | × | × | × | △ | △ | O | △ | △ | △ | O | △ |
| F HOME CARE STATION (RESPONSIBLE FOR MR. ARIMURA AT HOME) | × | × | × | × | × | × | × | × | × | × | × | × | △ | △ | △ | O |

INTEGRATED MULTI-FACILITY DOCUMENT MANAGEMENT SYSTEM

TECHNICAL FIELD

The present invention relates to an integrated multi-facility document management system that achieves smoothly coordinated activities among medical facilities, care facilities, and welfare facilities using an inter-facility access right management system in an electronic medical record system that efficiently creates and references records and work instruction documents of various document categories created for patients and residents at medical facilities, care facilities, and welfare facilities using a computer network, by enabling creating and referencing of consistent records and work instruction documents among the facilities and organizations even in a case where staff members in a wide variety of jobs intermix in a complicated manner between the facilities and organizations. Similarly, the present invention relates to an integrated multi-facility document management system including an inter-facility access right management system that, when multiple companies and organizations collaborate to carry out a project, manages the accessibility of instructions and records necessary for project progress, thereby enabling smooth information sharing among the companies and organizations.

BACKGROUND ART

As the number of elderly people in need of nursing care due to chronic disease or dementia has been increasing in recent years, it is becoming difficult to complete medical and nursing care only at a hospital or a care facility. A patient who has received treatment at a hospital due to pneumonia or a broken bone or the like is often unable to return to his/her home immediately after hospital discharge. In many cases, such a patient enters a care facility in the community, and, after the symptoms are alleviated, returns to his/her home or a home care facility while receiving home examination and home treatment and care provided by staff from a clinic in the community.

In this manner, a patient is transferred from a hospital or a clinic to a care facility and then to a home care facility or his/her home. Along with the transfer, people in a wide variety of jobs, such as doctors, nurses, rehabilitators, caregivers, and pharmacists, are involved in the medical and nursing care. The need to establish a so-called "community comprehensive care system", in which detailed information is shared among facilities and jobs, and organic, cooperative operations are performed, is now being suggested. In such a trend, it is inevitable to form an information sharing system such as an integrated multi-facility electronic medical record system that enables sharing of detailed information between facilities and jobs, and organic, cooperative operations.

Even in other fields, there are an increasing number of cases where companies and organizations collaborate to carry out the same project. Likewise, sharing detailed information among companies and organizations is indispensable to organic, cooperative operations.

In sharing information, it is essential to permit sufficient information access to staff members in need thereof, while at the same time refusing information access from other staff members to prevent leakage of personal information and confidential information of the company. For this purpose, it is necessary to strictly manage access rights.

In conventional information sharing, categories of documents that can be created and viewed are decided by the types of jobs such as doctors, nurses, and caregivers and the organization to which the staff members belong coincides with the facility where the staff members work, such as a hospital and a care facility. Accordingly, in a conventional staff-specific document-category-specific access right management table, access right management table for each job such as doctors, nurses, and caregivers is sufficient and is relatively simple as illustrated in FIG. 1. In the table, "○" indicates that a relevant document category can be created, edited and viewed, "Δ" indicates that a relevant document category only can be viewed, and "x" indicates that access is not allowed (creation, editing, and viewing are not allowed at all). Note that, although also there are forms of right such as a right to delete a document once created and an author right (a document creation is allowed but an editing right thereafter is limited to senior people), "○", "Δ", and "x" are solely exemplified herein for convenience of explanation.

In the table, a doctor article line refers to records and documents created by doctors and refers to medical records such as first visit doctor articles and doctor follow-up articles and statutory documents such as inpatient care plans and surgical consent forms. A doctor order line includes instruction prescriptions for staff members of each type of job, radiological examinations such as X-ray and CT, drug prescriptions, and rehabilitation instructions. A nursing article line includes data collection, planning, implementation records, and the like necessary for conducting nursing activities, such as nursing basic database, nursing care plans, and nursing daily reports. Care article line refers to assistive care records such as bathing and excretion performed by caregivers. These prescriptions and records have almost common content although names and the details of particulars change depending on facilities.

FIG. 2 illustrates facilities as places where services are provided and the document categories created in each facility by a tree-form structure. As illustrated in FIG. 2, facilities as places where medical services and care services are provided have become versatile in recent years as medical and nursing care fields are deployed throughout the community. Medical corporations that operate multiple facilities such as an A hospital and a B care facility are now becoming common. Places for providing services are expanding to pay nursing homes and own homes as well as hospitals and care facilities as in the past. In the pay nursing home, although the same building is used as a facility, each private room functions as an independent home. The number of medical corporations as upper organizations that manage multiple hospitals and care facilities is on the rise. In order to provide necessary medical services and care services, it is required to manage creation, viewing, and the like of the documents in the doctor article line, the doctor order line, the nursing article line, and the care article line for each facility and each home.

FIG. 3 illustrates organizations that provide services and staff members belonging to each service providing organization in a tree-form structure by type of job. In a conventional facility such as an A hospital or a B care facility, the facility as a place for providing services and the organization of staff members who provide services on that cite are united. The staff members of this organization will, in principle, provide services only to the facility as a place to which the staff members belong. In addition, it is quite unlikely that staff members of other organizations provide services to users who are hospitalized or reside in this facility. In contrast to this, services required by service users living at own homes scattered in the community are different from each other and there also are many cases where a plurality of organizations coexist as the service providers. For example, in the case of Mr. Arimura who lives at his own home, a medical doctor of a D home clinic, a nurse of an E home nursing station, a caregiver of an F home care station, and so on are involved. In some cases, a medical doctor in charge of him at an A hospital where he was originally hospitalized may conduct a home examination. Also in the pay nursing home, although the same building is used as a facility, each private room functions an independent home. Naturally, services required by each inmate are different from each other and these inmates concurrently receive services from different service providing organizations.

Documents such as instructions, plans, and implementation records accompanying the provided services are created by staff members of the provider organizations of the services. Meanwhile, the information in these documents must also be widely viewed and shared by staff members of other provider organizations that provide services to applicable service users at the same time. On the other hand, in the case of celebrity users, if the range of sharing information is inadvertently expanded, the risk of personal information leakage increases. Accordingly, it is appropriate to prohibit all general staff members from access and limit the sharing range to individual levels of staff members who directly provide services.

As described thus far, in a case where a place for providing services and an organization as the service provider are united, simple access right management as illustrated in FIG. 1 is sufficient. However, when multiple types of jobs such as doctors, nurses, caregivers, and the like who belong to different organizations as the service providers are involved at places for providing services in various forms such as pay nursing homes and own homes, furthermore, at different levels for each individual, complicated access right management is inevitable, for example, as indicated by a staff-specific facility-specific document-category-specific access right management table in FIG. 4.

In FIG. 4, a medical doctor with a staff ID 0943 is working at the A hospital but also conducts a home examination on Mr. Arimura who is at home under medical treatment. At the A hospital, this medical doctor creates documents in the doctor article line and the doctor order line and views nursing line articles and care line articles as a medical doctor responsible for inpatients. Regarding residents of the B care facility which is an allied facility of the same corporation, the medical doctor is allowed to view all the documents but, since the medical doctor is not responsible for the residents, there is no right to create documents. With respect to a C pay nursing home, the medical doctor is not in charge thereof and thus cannot access any documents, including documents in the doctor article line and the doctor order line. Regarding Mr. Arimura who is at home under medical treatment, since the medical doctor concurrently serves as a medical doctor responsible for the home examination, the medical doctor has the same access right as that in the A hospital.

Since a medical doctor of a C home clinic having a staff ID 1285 does not belong to a medical corporation xx society, this medical doctor has no access right regarding the A hospital and the B care facility at all. Regarding Mr. Yamada in the C pay nursing home, of whom this medical doctor is in charge, this medical doctor has a right to create documents in the doctor article line and the doctor order line and a right to view nursing line articles and care line articles. Regarding Mr. Arimura who is at home under medical treatment, this medical doctor is not in charge of him and thus has no access right.

A nurse of the A hospital having a staff ID 2513 has a right to create nursing line articles of the A hospital to which the nurse directly belong and a right to view documents of hospitals and facilities participating in the medical corporation xx society but cannot access any documents regarding the C pay nursing home outside the corporation and own homes.

A nurse with a staff ID number 4165 belonging to the E home nursing station does not belong to the medical corporation xx society and thus has no access right regarding the A hospital and the B care facility at all. Regarding Mr. Yamada in the C pay nursing home and Mr. Arimura who is at home under medical treatment, of whom this nurse is in charge, this nurse has a right to create documents in the nursing article line and a right to view documents in the doctor article line, the doctor order line, and the care line.

A caregiver of the F home care station having a staff ID 7156 is in charge of Mr. Arimura who is at home under medical treatment. Since this caregiver does not belong to the medical corporation xx society, the caregiver has no access right regarding the A hospital and the B care facility at all similarly to the case regarding Mr. Yamada in the C pay nursing home, of whom the caregiver is not in charge. Regarding Mr. Arimura who is at home under medical treatment, of whom the caregiver is in charge, the caregiver has a right to create documents in the care article line and a right to view documents in the doctor article line, the doctor order line, and the nursing line. The caregiver of the A hospital is not allowed to view documents in the doctor article line and the doctor order line as illustrated in FIG. 1 but is allowed to view documents regarding Mr. Arimura who is at home under medical treatment. As described above, the range of permitting the viewing right is not uniquely decided by the types of jobs but is determined in accordance with the situation.

As described thus far, in the current access right management, a place for providing services and an organization as the service provider are combined in a complicated manner and additionally, these combinations are constantly changing. Conventionally, an administrator has manually set the staff-specific facility-specific document-category-specific access right management table as illustrated in FIG. 4 one by one. In addition to being troublesome and time-consuming, setting errors tend to occur, frequently causing disadvantages such as not being able to access a document supposed to be accessed and not being able to smoothly carry out the task, or conversely, leading to leakage of personal information through a staff member who is not supposed to access the document by viewing the document.

CITATION LIST

In order to save time and effort of managing the access rights of documents and files, operating systems (OSs) such as UNIX and WINDOWS have used for a long time a file management technique that arranges files and directories containing files in a tree form and causes the access right to be inherited from a root directory toward branches and leaves. An access right set in a directory serving as a parent directory is automatically inherited to a child directory created within the parent directory (a trunk or a branch). The access right set for each directory is applied to a file (leaf) in that directory. This facilitates consistent management of access rights and accordingly, this technique is still used as a standard technique for file access right management.

Technologies disclosed in Patent Literatures 1 and 2 have been proposed as publications related to such a technology but, in both cases, the access right is inherited in file directories having a relationship between parent and child.

In addition, the technologies of Patent Literatures 3 and 4 have also been proposed.

CITATION LIST

Patent Literature

Patent Literature 1: JP 2000-207336 A
Patent Literature 2: JP 2006-085356 A
Patent Literature 3: JP 2009-070206 A
Patent Literature 4: JP 2007-233635 A In Patent Literature 3, when a user makes access, the access right of an upper directory is dynamically searched for to check whether this user has an access privilege thereof. This eliminates the need to manually modify the access right to lower directories. Meanwhile, Patent Literature 4 makes it easy to add, modify, and delete the access right by performing a process called filtering on a standard access right pattern.

SUMMARY OF INVENTION

Technical Problem

The file management technique of the OSs and the Patent Literatures 1 and 2 have the following disadvantages.
(1) Because the access right is inherited only when the child directory is created, even if the access right of the parent directory is modified at a later point in time, the modification is not automatically reflected to a descendant directory. Updating the access right of the descendant directory requires manual modification and not only a large amount of work is required but also there is a risk of inconsistency occurring due to a work error.
(2) For access right management by staff, it is necessary to create a tree-form representation of document access right for each group (role) of staff members who have the same responsibility and complicated setting as illustrated in FIG. 4 requires a very difficult work.

In Patent Literatures 3 and 4, updating the access right of descendant directories is somewhat easier but disadvantage (2) "for access right management by staff, it is necessary to create a tree-form representation of document access right for each group (role) of staff members who have the same responsibility and complicated setting as illustrated in FIG. 4 requires a very difficult work" is still unresolved.

The present invention has been made to solve the above disadvantages of conventional technologies, and an object of the present invention is to provide an integrated multi-facility document management system that achieves smoothly coordinated activities among medical facilities, care facilities, and welfare facilities by easily performing consistent access right management among multiple facilities and different service providing organizations and enabling referencing, creating, editing, and deleting of records and work instruction documents while maintaining consistency even in a case where a large number of the facilities and the service providing organizations coexist, where a policy of document access right differs for each facility, and where staff members in a wide variety of jobs intermix in a complicated manner between the facilities and the organizations.

Similarly, an object of the present invention is to provide an integrated multi-facility document management system including an inter-department access right management system that, when multiple companies and departments collaborate to carry out a project, manages the accessibility of instructions and records necessary for project progress, thereby enabling smooth information sharing among the companies and organizations.

Solution to Problem

An integrated multi-facility document management system according to claim 1 of the present invention, as a means for attaining the object, includes:
a facility-specific user ID managing unit that manages IDs of facility users at each facility among a plurality of facilities; a facility-specific document category managing unit that manages document categories being used at the facilities; a facility-specific document-category-specific document recording unit that records document data for each document category at each facility; a facility-specific document-category-specific access right managing unit that manages access rights of staff for each document category at each facility; and a staff login authenticating unit that authenticates access rights of staff, in which
the facility-specific document-category-specific access right managing unit includes:
a document category tree-form layout representation unit in which document categories for each facility are laid out and represented in a tree form; a staff tree-form layout representation unit in which staff members are laid out and represented in a tree form for each organization; and a tree-form-layout-representation-pair association setting unit that associates a tree-form layout representation pair of the document category tree-form layout representation and the staff tree-form layout representation with each other,
the integrated multi-facility document management system further including an access right managing unit using the tree-form layout representation, the access right managing unit enabling visible and efficient management of access rights for each document category at each facility by causing access right attributes to be inherited from a root of the tree-form layout representation pair in a branch direction.

An integrated multi-facility document management system according to claim 2 is the integrated multi-facility document management system according to claim 1, in which the tree-form-layout-representation-pair association setting unit includes an inter-tree-form-layout-representation-pair object operating unit that sets an association relationship between the tree-form layout representation pair with a drag-and-drop operation between objects of the tree-form layout representation pair.

An integrated multi-facility document management system according to claim 3 is the integrated multi-facility document management system according to claim 1 or 2, in which the access right managing unit using the tree-form layout representation includes an access right management table synchronizing unit that synchronizes contents of access right management using the tree-form layout representation, for which association between the tree-form layout representation pair has been set, to at least one of a staff-specific facility-specific document-category-specific access right management table and a facility-specific document-category-specific staff-specific access right management table.

Advantageous Effects of Invention

In the integrated multi-facility document management system according to claim 1 of the present invention, since the facility-specific document-category-specific access right managing unit is provided with the document category tree-form layout representation unit in which document categories for each facility are laid out and represented in a tree form, documents being used at each facility are classified into categories and listed.

Since the facility-specific document-category-specific access right managing unit is provided with the staff tree-form layout representation unit in which staff members are laid out and represented in a tree form for each organization, staff members belonging to each organization is listed and displayed.

Since the facility-specific document-category-specific access right managing unit is provided with the tree-form-layout-representation-pair association setting unit that associates the tree-form layout representation pair of the document category tree-form layout representation and the staff tree-form layout representation with each other, documents for which creating, editing, and referencing are allowed are identified for doctors, nurses, caregivers, and the like belonging to each organization.

Since there is provided the access right managing unit using the tree-form layout representation, which enables visible and efficient management of access rights for each document category at each facility by causing the access right attributes to be inherited from the root of the tree-form layout representation pair in the branch direction, an access right according to a mode such as creation, editing, and deletion is easily set in accordance with the facility and the type of job of a staff member.

Since the integrated multi-facility document management system according to claim 2 of the present invention is provided with the inter-tree-form-layout-representation-pair object operating unit, an easy and reliable operation environment by a drag-and-drop operation is achieved.

In the integrated multi-facility document management system according to claim 3, since the access right managing unit using the tree-form layout representation is provided with the access right management table synchronizing unit that synchronizes contents of access right management using the tree-form layout representation, for which association between the tree-form layout representation pair has been set, to at least one of the staff-specific facility-specific document-category-specific access right management table and the facility-specific document-category-specific staff-specific access right management table, it is possible to quickly judge whether to allow access by referencing the access right management table when distinguishing access.

BRIEF DESCRIPTION OF DRAWINGS

FIG. 1 is an explanatory diagram of a conventional staff-specific document-category-specific access right management table.

FIG. 4 is an explanatory diagram of a staff-specific facility-specific document-category-specific access right management table based on FIGS. 2 and 3.

DESCRIPTION OF EMBODIMENTS

Embodiment

Figure 5:
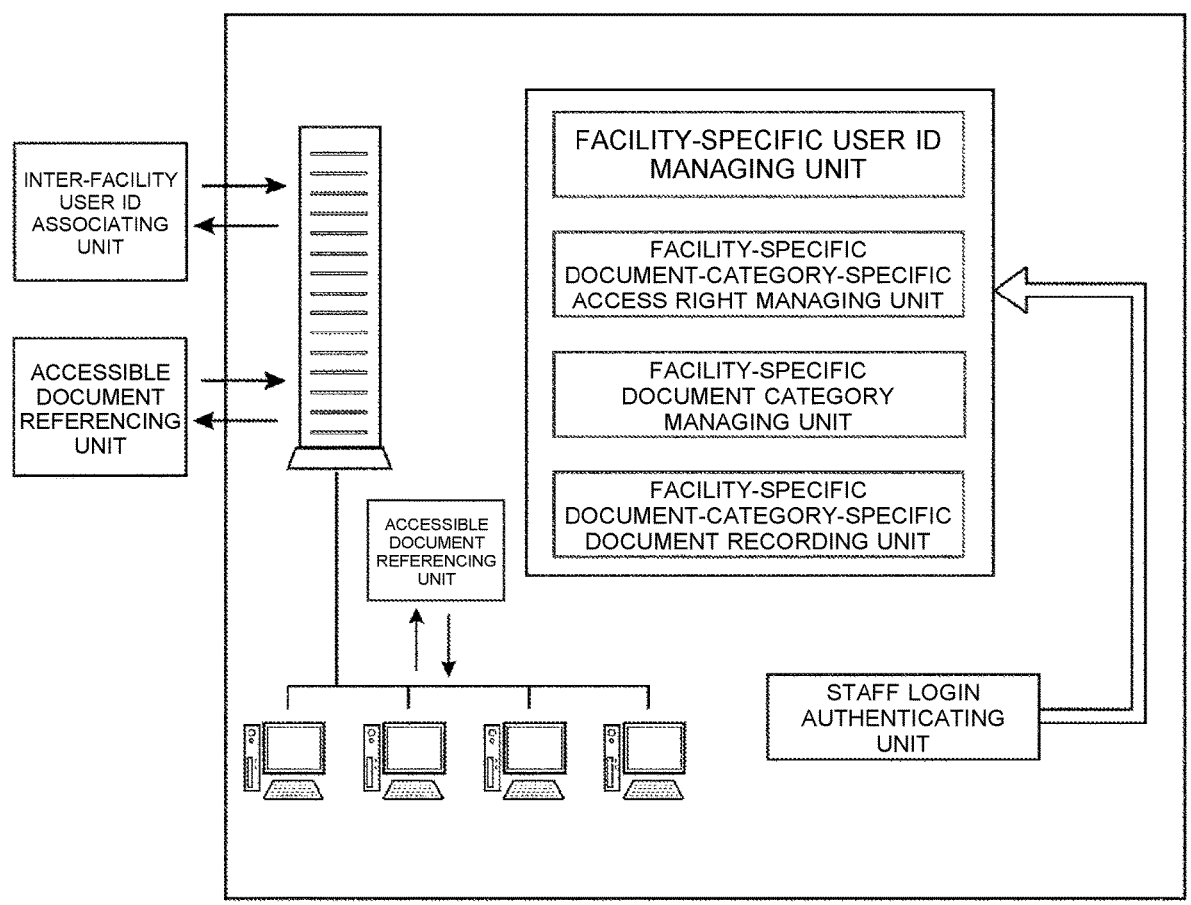
FIG. 5 is an explanatory diagram illustrating the configuration of the inside of a facility in the configuration of an entire integrated multi-facility document management system of the present invention.

FIG. 5 illustrates the configuration of the inside of a facility in the configuration of an entire integrated multi-facility document management system of the present invention. At each facility, there is a facility-specific user ID managing unit that manages the IDs of users who use the facility. The facility-specific user ID managing unit is an inpatient list and an outpatient list at a hospital, is a resident list at a facility, and is a visit destination list or the like in a visit service. For ease of use, each list is in room number order, alphabetical order, ID number order, or the like.

In the facility-specific user ID managing unit, user IDs may be defined at each facility as in a conventional case. In such a case, however, there is a need to create and manage a user ID correspondence table between facilities, to associate and manage the same person with different user IDs between facilities (an inter-facility user ID associating unit). Meanwhile, Medical IDs (provisional name) that are currently considered are unique IDs that can be used throughout the nation, and accordingly, can be shared at all facilities. Thus, the inter-facility user ID associating unit becomes unnecessary, which is the most preferable aspect. The next best measure is to use user IDs that are shared among the respective facilities in the same legal entity. In this case, the above mentioned inter-facility user ID associating unit is used to associate the user IDs with user IDs being used at facilities outside the legal entity.

Further, document categories at each facility and particulars (form definitions) of each document category are determined in accordance with the services being provided at each individual facility. A list of the names of the document categories and information about the particulars of each document category are recorded and managed by a facility-specific document category managing unit. A document in a designated document category is created or edited in accordance with the information about the particulars of the document category. The created or edited document is recorded by a facility-specific document-category-specific recording unit of the document category.

At each facility, combinations of rights of access to the respective document categories, such as document categories that can be created and edited, document categories that can only be referenced, and document categories that are not allowed even to be referenced, vary depending on the affiliation and the types of jobs of the staff members. In a facility-specific document-category-specific access right managing unit, the management table shown in FIG. 4 is created, and access rights are managed for each staff member and each document category. Here, "○" indicates that creation, edit, and reference are allowed, "Δ" indicates that only reference is allowed, and "x" indicates that even reference is not allowed. For example, a medical doctor who works at the facility can create, edit, and reference doctor-related article documents and documented medical work instructions and prescriptions (order documents), but can only reference articles for the other types of jobs such as nurses and caregivers. As for the doctor articles and the order documents of a facility at which a certain medical doctor is not working, the medical doctor can reference a range of document categories allowed by the facility (or for which an access right is given to the medical doctor), but cannot create or edit any document.

As a staff ID and a password or a biometric identification or the like is input from a terminal, the staff member is authenticated (a staff login authenticating unit). As the staff member is authenticated, the access rights of the staff member in each document category are made clear by the facility-specific document-category-specific access right managing unit. In response to an access request to create, edit, or reference a document category designated by the staff member, the access is allowed if the staff member has the right to do so, but the request is rejected if the staff member does not have the right.

For ease of explanation, the facility-specific user ID managing unit, the inter-facility user ID associating unit, the facility-specific document category managing unit, the facility-specific document-category-specific recording unit, the facility-specific document-category-specific access right managing unit, and the staff login authenticating unit are mounted in a server in a facility in this example, but some or all of them may be gathered in the central server and be connected by a communication line such as the Internet. In the central server, the respective facility systems may be mounted in the respective physical servers separately from one another, or virtual servers may be formed by logically dividing the same physical server. Further, an actual server may not be formed, and a cloud service may be used in the form of SaaS.

Medical or care facilities manage a staff list in the form of a list of employees or the like at each facility. All the records of the medical and nursing care services provided by staff members, including the information gathering and the planning, are managed at each facility. A patient is transferred from an acute hospital to a recovery hospital to a care facility to a home care service, in accordance with stages of disease. Documents created in relation to medical and nursing care are created, edited, or deleted at the facility to which the patient has been transferred (a principal facility), and should then be saved and managed. The staff members providing medical and nursing care services to the patient need to have rights to create, edit, or delete documents at the principal facility, and need to create, edit, or delete documents with the rights.

In a case where the facility to which a patient is to be transferred (the next "principal facility") has already been decided, documents in relation to medical and nursing care of future dates after the transfer should be created at the next principal facility to which the patient is to be transferred, instead of the current principal facility. For this reason, to create, edit, and delete documents at future principal facilities as well as the current principal facility, it is only necessary to designate a principal facility such that a right to create, edit, or delete documents at the facility is authenticated through the staff login authenticating unit.

Staff login authentication may not be performed directly on the principal facility, but additional login authentication may be performed on another necessary principal facility after the staff member has logged in at the principal facility. If the same staff ID and the same password are used, the additional login authentication is automatically performed. In such a case, there is a possibility of security becoming slightly weaker. Therefore, depending on the adopted operation policy, the same staff member may have a different staff ID and a different password at each principal facility. After staff login authentication is performed at the principal facility, access rights in the respective document categories are given in accordance with FIG. 4.

Every time a document is created, edited, or deleted, a principal facility may be designated, and staff login authentication at the facility may be performed as necessary. At the present time, however, the login process at every time at a principal facility to which a patient has been further transferred is often complicated. In order to avoid this process, by creating a table that manages the principal facilities at the present time, and if necessary, the principal facilities of the future date, for each user, it is possible to identify an applicable principal facility once the user ID and a desired date of creating, editing, and deleting a document are designated. If staff login authentication has not been performed on the corresponding principal facility, additional staff login authentication should be performed so that the document can be smoothly created, edited, or deleted.

Conventionally, facilities as places for providing services (for example, hospitals, nursing healthcare facilities, and special nursing care homes) and staff members who provide services there were united. Therefore, all the documents created in the facility were created by the staff of the facility. Accordingly, giving access rights to the staff for each document category was relatively simple as illustrated in FIG. 1.

At present time, however, as the number of elderly people and people in need of nursing care increases, the number of people receiving home care services such as home examination, home nursing, and home care at pay nursing homes and at own homes has been increasing. These home care services are provided by staff members belonging to a service providing agency that is separate from the facility as a place such as the pay nursing home or own home, including a home support clinic, a home nursing station, and a home care station. These service providing agencies provide services to facilities as multiple places. The relevant service providing agencies have obligation to manage documents created because of the provision of services in a first meaning but, at the same time, it is necessary that documents that have been created for multiple provided services can be browsed for each user who receives multiple services at each facility.

Meanwhile, as described earlier, in facilities such as own homes, staff members of multiple facilities come and leave at all times to perform medical and nursing care but, from the viewpoint of staff members, they are involved in tasks at multiple facilities. For example, in the case of the medical doctor, there is a case where a medical doctor serves as a full-time doctor at a certain hospital and visits a patient's home, while at the same time serving as a part-time doctor at another dedicated home clinic and visiting a care facility from this clinic to conduct home examination.

As described thus far, the management of document access rights in performing community comprehensive care becomes extremely complicated in the conventional manner and it is likely to lead to accidents such as confusion and leakage of personal information.

Figure 2:
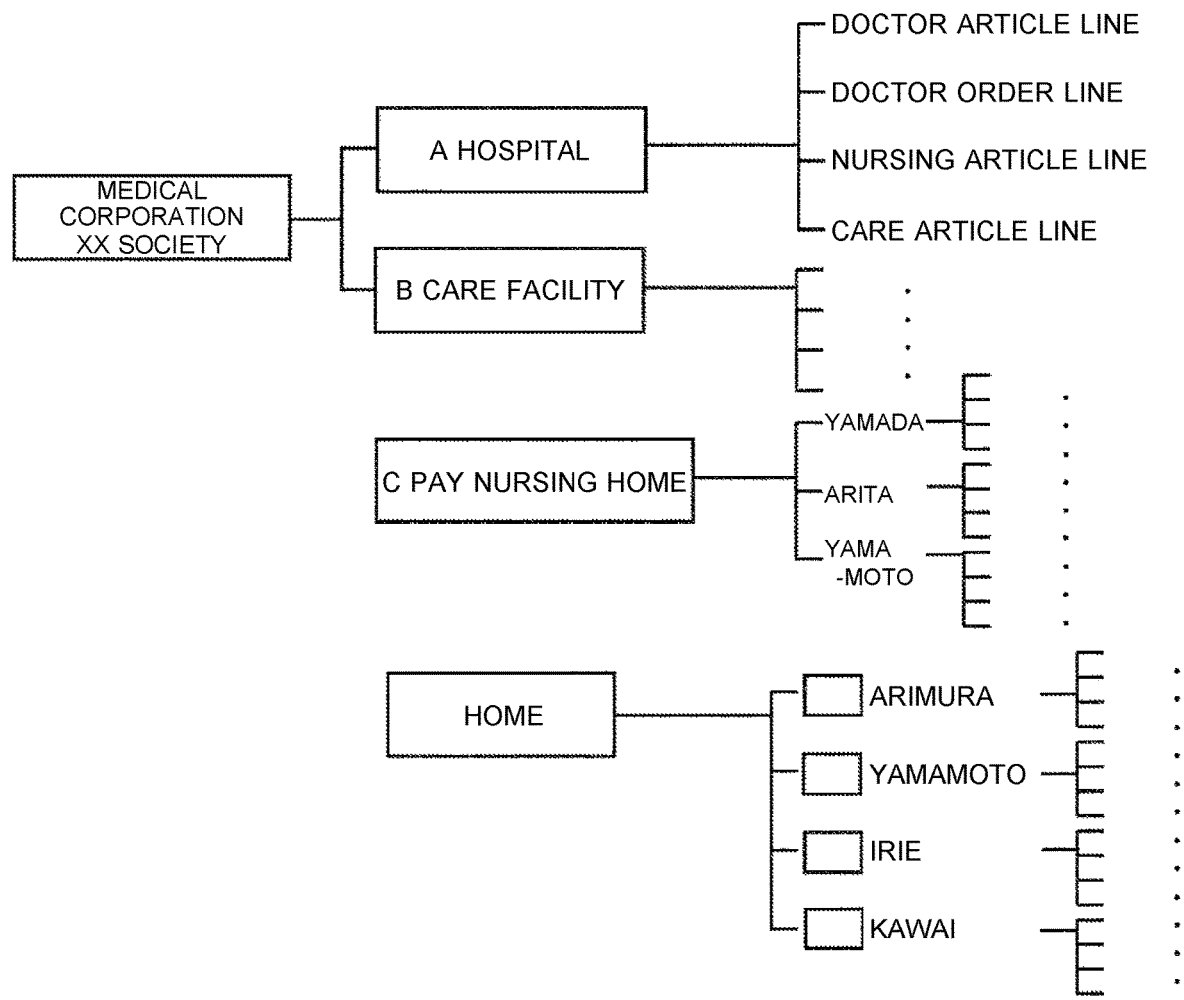
FIG. 2 is a diagram illustrating facilities as places for providing services and document categories created in each facility in a tree-form structure (document category tree-form layout representation unit).

FIG. 2 is a diagram illustrating facilities as places for providing services and document categories created in each facility in a tree-form structure (document category tree-form layout representation unit). In the present invention, tree-form structure data is created with a nested structure of XML tags but is not limited to XML as long as the same tree-form structure can be represented. When a large number of document categories are used, sub-categories may be prepared in such a manner that document categories treated similarly are collected as a group such as "doctor article line" or "doctor order line" as illustrated in FIG. 1.

Figure 3:
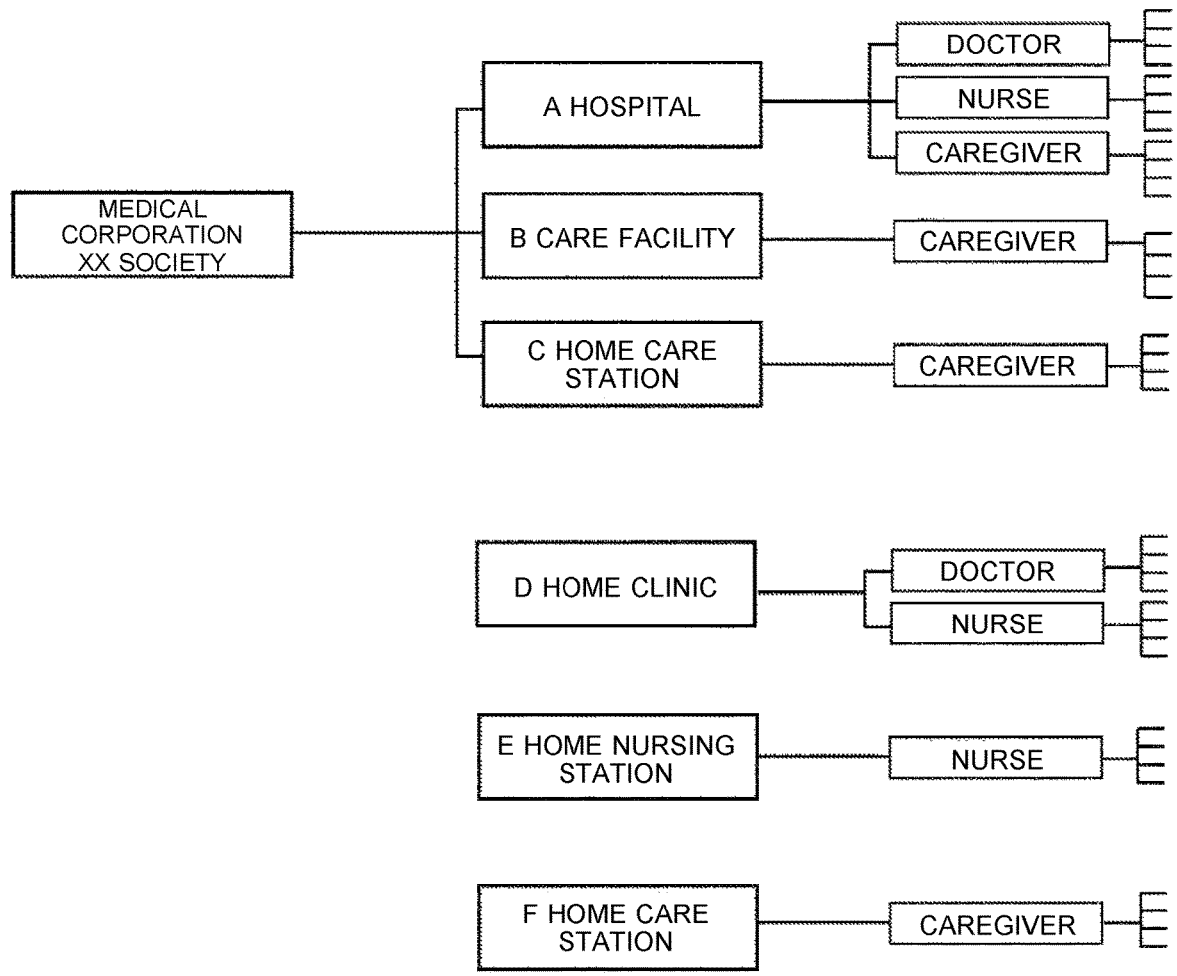
FIG. 3 is a diagram illustrating organizations that provide services and staff members belonging to each service providing organization in a tree-form structure by type of job (staff tree-form layout representation unit).

FIG. 3 is a diagram illustrating agencies that provide services and staff members belonging to each service providing agency in a tree-form structure (staff tree-form layout representation unit). Similarly, tree-form structure data is created with a nested structure of XML tags but is not limited to XML as long as the same tree-form structure can be represented. When there is a large number of affiliated staff members, sub-categories may be prepared in such a manner that staff members of types of jobs treated similarly are collected as a group such as "doctors", "nurses", and "caregivers".

Figure 6:
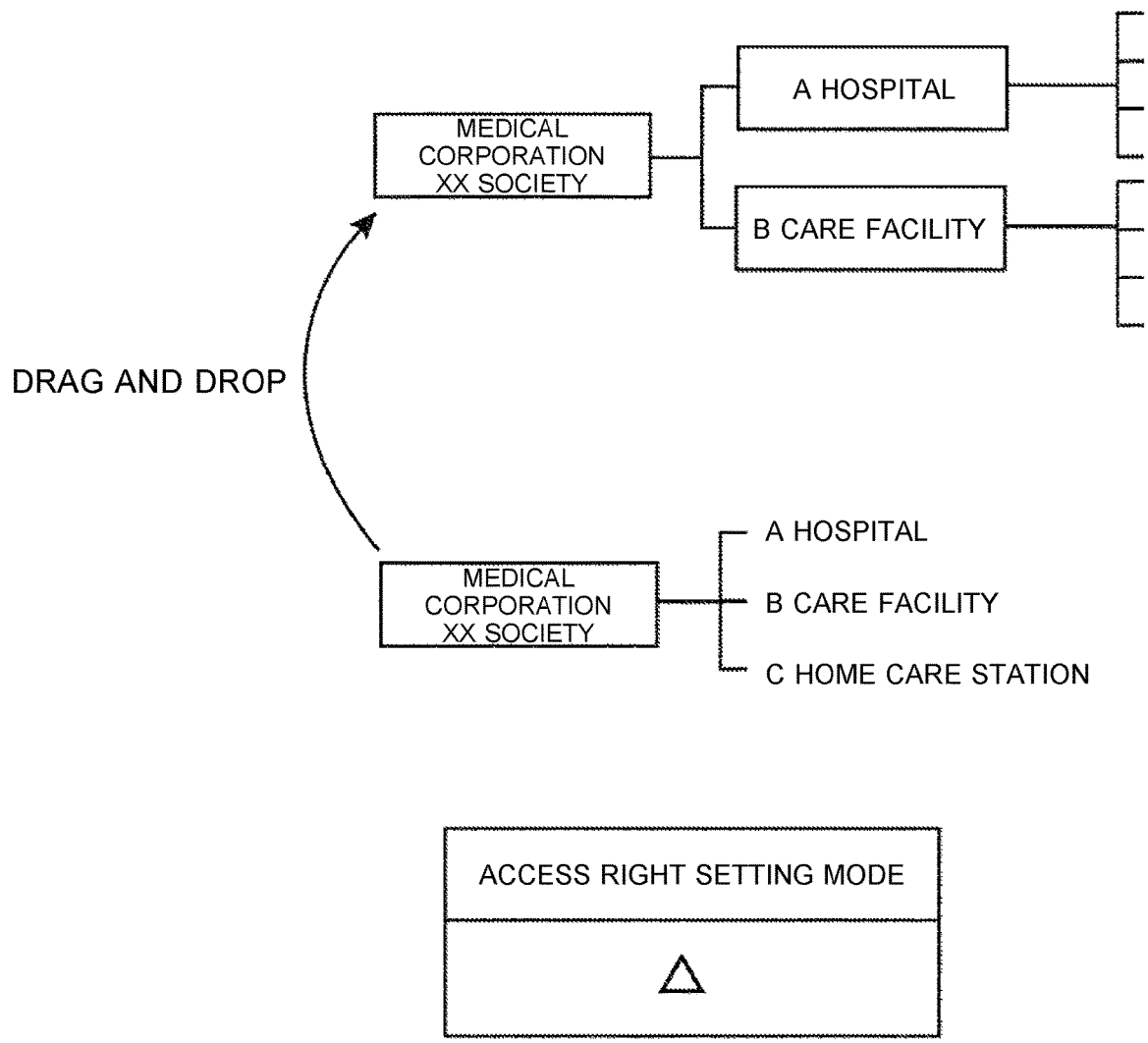
FIG. 6 is an explanatory diagram of access right setting ("Δ") by dragging and dropping an object.
Figure 7:
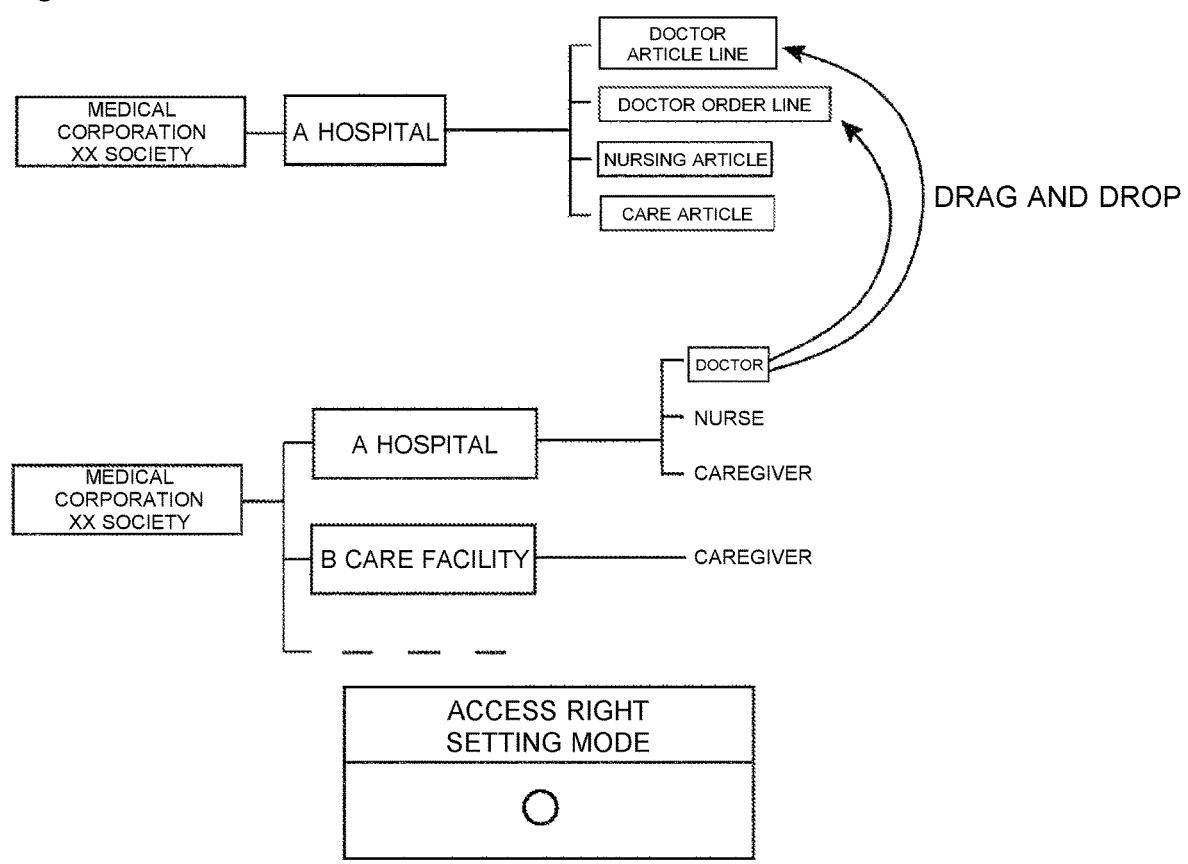
FIG. 7 is an explanatory diagram of access right setting ("○") by dragging and dropping an object.

Each of FIGS. 6 and 7 illustrates an example of a tree-form-layout-representation-pair association setting unit that associates a tree-form layout representation pair of the tree-form structure of the document categories illustrated in FIG. 2 and the tree-form structure of the service-providing-agency-affiliated staff members illustrated in FIG. 3 with each other. An access right setting mode "Δ" in the lower left of FIG. 6 indicates that association setting is performed for setting that allows only reference. When setting is made so as to allow all the staff members of the xx corporation to reference documents of all the allied facilities of the xx corporation, it is only required to drag and drop the object of the xx corporation of the tree-form structure of the service-agency-affiliated staff members onto the object of the xx corporation of the tree-form structure of the document categories. An accessible right attribute dropped on an upper order (in a root direction) of the tree-form structure is inherited to lower orders (in a leaf direction) of the tree-form structure (an example of the tree-form-layout-representation-pair association setting unit).

Subsequently, the access right setting mode in the lower left of FIG. 7 is changed to "○" and a sub-category object of "doctors" belonging to each service providing agency is dragged and dropped onto sub-category objects of "doctor article" and "doctor order" of a facility to which services are provided, whereby, the initial "Δ" is overwritten with "○" as the access right of the doctors for these document sub-categories and rights to create, edit, and delete are assigned thereto. In a facility where these doctors are not working and do not provide services, the access right remains at the initial "Δ". Similarly, "○" is assigned to the nurses for documents in the nursing article line of a facility to which services are provided, while "○" is assigned to the caregivers for documents in the care article line of a facility to which services are provided.

As for the patient Arimura's home where home examination by the A hospital and visiting services by the C home nursing station from the xx corporation are provided and, regarding nursing care, visiting services by the F home care station outside the corporation are provided, first in the access right setting mode of "Δ", each object of the A hospital home examination department and the home nursing station of the xx corporation and the F home care station outside the corporation is dragged and dropped onto the object of the patient Arimura's home. As a result, documents in relation to the patient Arimura's home can be referenced among the staff members of the A hospital home examination department and the C home nursing station of the xx corporation and the staff members of the F home care station outside the corporation. Next, the access right setting mode is changed to "○" and each object of the A hospital home examination department and the C home nursing station of the xx corporation and the F home care station outside the corporation are dragged and dropped individually onto the respective objects of the doctor articles, the doctor orders, the nursing article line, and the care article line for the patient Arimura's home, whereby rights to create, edit, and delete documents corresponding to the types of jobs are obtained. What access right is granted to which staff member can be arbitrarily set by the operational strategy.

For example, regarding documents of a patient requiring top-secret security, it is possible not to allow reference to the documents at all except for staff members who have been granted a special mission. In this case, a separate object of a special room is created as a different facility in the tree-form structure of the document categories and all the document categories are expanded into branches and leaves. After the access right setting mode is adjusted to "x" and access to all the document categories is temporarily prohibited for all the staff members, reference to the entire documents of the special room is permitted to each specific staff member ("Δ" mode) and then, creation, editing, and deletion rights are given to the document categories in accordance with the types of jobs ("○" mode), whereby setting is enabled. Conversely, it is also possible to grant the reference right of the facility documents, which is not ordinarily granted, to specific staff in charge of auditing.

In the above-described access right managing unit using the tree-form layout representation, the inheritance of the accessible right attribute may be used in each case in response to an access request while the tree-form layout representation is maintained as it is such that the access right of the staff to the document category is authenticated. However, it requires a lot of calculation and takes time. In order to prevent this, by updating the access right management table that lists the access rights of each staff for each document category as illustrated in FIG. 4 every time the tree-form-layout-representation-pair association setting unit is executed, it is possible to quickly judge whether to allow access upon the access request by referencing the access right management table. In some cases, the access right management table may be updated at once after setting by the tree-form-layout-representation-pair association setting unit is completed. In addition, the access right table can be not only the above-mentioned access right list for each staff member for each document-category but also an accessible staff list for each document category. Both of the lists may be appropriately used in combination.

Here, as an example, the tree-form-layout-representation-pair association setting unit is achieved by dragging and dropping the staff object onto the document category object, but conversely, may be achieved by dragging and dropping the document category object onto the staff object. In addition, although the operability is inferior, the association may be similarly set by keyboard operation using a function key, a pull-down menu, or the like without using object operation.

Although an embodiment has been described so far, specific structures of the present invention are not limited to the above embodiment, and design changes and the like within the scope of the invention are included in the present invention.

For example, in the above-described embodiment, the hospitals and the care facilities are described as an example, but the present invention is not limited thereto. Companies and organizations can employ an inter-facility access right management system that manages the accessibility of instructions and records necessary for project progress so as to operate the inter-facility access right management system among the companies and organizations.

The invention claimed is:

1. An integrated multi-facility document management system comprising:
   computers that are installed in a plurality of facilities;
   a central server in electronic communication with the computers of the facilities, the central server including a processor and a storage device;
   the storage device comprising instructions, which when executed by the processor, cause the processor to: manage identifications of facility users at the facilities; manage document categories being used at the facilities; record document data for each document category at each facility; manage access rights of staff for each document category at each facility; and authenticate access rights of staff, wherein
   the instructions further cause the processor to manage the access rights of staff for each document category at each facility including:
   a document category tree-form layout in which document categories for each facility are displayed in a first tree form together with a staff tree-form layout in which members of the staff for each facility are displayed in a second tree form;
   the instructions further cause the processor to: allow a first access right attribute to be dragged and dropped from the second tree form to a first root of the first tree form whereby when the first access right attribute is dragged and dropped from the second tree form to the first root of the first tree form a corresponding access right attribute of the first root is automatically changed to the first access right attribute and a corresponding access right attribute in branches connected to the first root is automatically changed to the first access right attribute, or allow a second access right attribute to be dragged and dropped from the first tree form to a second root of the second tree form whereby when the second access right attribute is dragged and dropped from the first tree form to the second root of the second tree form a corresponding access right attribute of the second root is automatically changed to the second access right attribute and a corresponding access right attribute in branches connected to the second root is automatically changed to the second access right attribute.

2. The integrated multi-facility document management system according to claim 1, wherein
   the instructions further cause the processor to generate a staff-specific facility-specific document-category-specific access right management table based on the document category tree-form layout and the staff tree-form layout.

3. The integrated multi-facility document management system according to claim 1, wherein the staff tree-form layout that is displayed includes the facilities and the members of the staff associated with each facility.

4. The integrated multi-facility document management system according to claim 2, wherein the staff-specific facility-specific document-category-specific access right management table includes the facilities, the document categories, the members of the staff, and the access rights.

* * * * *